United States Patent
Wachernig (10) Patent No.: US 12,405,266 B2
(45) Date of Patent: Sep. 2, 2025

(54) METHOD FOR DETERMINING THE NUMBER OF ANTIBODIES ON EXOSOMES USING QUALITY CONTROL ACCORDING TO A FIRST METHOD OF DESIGN RECOGNITION AND ACCORDING TO A SECOND METHOD OF ELECTROPHORESIS

(71) Applicant: PARTICLE METRIX GMBH, Inning am Ammersee (DE)

(72) Inventor: Hanno Wachernig, Diessen a. A. (DE)

(73) Assignee: PARTICLE METRIX GMBH, Inning am Ammersee (DE)

(*) Notice: Subject to any disclaimer, the term of this patent is extended or adjusted under 35 U.S.C. 154(b) by 831 days.

(21) Appl. No.: 17/607,988

(22) PCT Filed: Apr. 27, 2020

(86) PCT No.: PCT/DE2020/000083
§ 371 (c)(1),
(2) Date: Nov. 1, 2021

(87) PCT Pub. No.: WO2020/221382
PCT Pub. Date: Nov. 5, 2020

(65) Prior Publication Data
US 2022/0341917 A1    Oct. 27, 2022

(30) Foreign Application Priority Data
May 2, 2019    (DE) .................... 10 2019 003 132.6

(51) Int. Cl.
*G01N 33/50*     (2006.01)
*G01N 21/64*     (2006.01)
*G01N 33/53*     (2006.01)

(52) U.S. Cl.
CPC ..... *G01N 33/5076* (2013.01); *G01N 21/6456* (2013.01); *G01N 33/5308* (2013.01)

(58) Field of Classification Search
CPC ....... G01N 15/01; G01N 15/06; G01N 15/075; G01N 2015/0038; G01N 21/6456; G01N 33/5076; G01N 33/5308
See application file for complete search history.

(56) References Cited

U.S. PATENT DOCUMENTS

2017/0045451 A1   2/2017   Nolan
2019/0277743 A1   9/2019   Wachering

FOREIGN PATENT DOCUMENTS

DE     202018005287       1/2019
TW     201639966 A   *   11/2016

OTHER PUBLICATIONS

English Machine Translation of TW-201639966-A (Year: 2016).*
Akagi, T., et al., "On-Chip Immunoelectrophoresis of Extracellular Vesicles Released from Human Breast Cancer Cells", PLOS ONE, Apr. 30, 2015, 10(4): e0123603. doi:10.1371/journal.pone.0123603.

(Continued)

*Primary Examiner* — Gurpreet Kaur
(74) *Attorney, Agent, or Firm* — Duane Morris LLP; Gregory M. Lefkowitz; Brandon A. Chan (57) ABSTRACT

The invention relates to a method for determining the florescence of antibodies on exosomes using quality control of the measurement using two different control methods.

12 Claims, 6 Drawing Sheets

(56) References Cited

OTHER PUBLICATIONS

Pugholm, L.H., et al., "Antibody-Based Assays for Phenotyping of Extracellular Vesicles", Biomed Research International, Jan. 1, 2015, vol. 2015, Article ID 524817, 15 pages, http://dx.doi.org/10.1155/2015/524817.

Hartjes, T., et al., "Extracellular Vesicle Quantification and Characterization: Common Methods and Emerging Approaches", Bioengineering, Jan. 2019, vol. 6, No. 7, doi: 10.3390/bioengineering6010007.

Helmbrecht, C., et al., "High efficiency quantification of fluorescent labeled EVs with F-NTA", May 17, 2017, Retrieved from: https://www.particle-metrix.de/fileadmin/pdf_technologien/Poster_A0_Fluorescence_EN.pdf.

Helmbrecht, C., et al., "Surface Charge and Pattern Analysis - Differentiating Tools in Scanning NTA", May 17, 2017, Retrieved from: https://www.particle-metrix.de/fileadmin/pdf_technologien/Poster_AO_Surface_Charge_Pattern_EN.pdf.

Anonymous, "Zetapotential Bestimmung mit Hilfe der Elektrophorese-Methode (Zeta potential determination using the electrophoresis method", Nov. 30, 2015, Technologies—Particulate Charge, Particle Metrix, Retrieved from: https://www.particle-metrix.de/technologien/nanopartikel-tracking/artikel-nanopartikel-tracking/zetapotential-bestimmung-mit-hilfe-der-elektrophorese-methode.

Helmbrecht, C., et al., "Standardizing F-NTA measurements", Apr. 17, 2019, Retrieved from: https://www.particle-metrix.de/fileadmin/pdf_applications/SciencePoster%20ISEV2019_A4_010_print.pdf.

Bachurski, D. et al., "Extracellular vesicle measurements with nanoparticle tracking analysis—An accuracy and repeatability comparison between NanoSight NS300 and ZetaView", Journal of Extracellular Vesicles, 2019, vol. 8, 1596016.

\* cited by examiner

METHOD FOR DETERMINING THE NUMBER OF ANTIBODIES ON EXOSOMES USING QUALITY CONTROL ACCORDING TO A FIRST METHOD OF DESIGN RECOGNITION AND ACCORDING TO A SECOND METHOD OF ELECTROPHORESIS

CROSS-REFERENCE TO RELATED APPLICATIONS

This application is a § 371 national stage entry of International Application No. PCT/DE2020/000083, filed on Apr. 27, 2020, which claims priority to German Patent Application No. 10 2019 003 132.6, filed on May 2, 2019, the entire contents of which are incorporated herein by reference.

The application relates to a method for determining the fluorescence and the number of antibodies on exosomes using a quality control by a first method of pattern recognition and by a second method of electrophoresis.

In biology, vesicles are very small, round to oval, intracellular bubbles which are surrounded by a monolayer or bilayer membrane or a reticulated shell of proteins. Vesicles form their own cell compartment, in which different cellular processes take place. Their size is about one micrometer. Vesicles are responsible for the transport of many substances in the cell.

The mechanisms which lead to the formation of extracellular vesicles have not yet been fully clarified.

Here, exosomes are small vesicles having a size of approx. 50 to 150 nm.

Extracellular vesicles play a major role in intercellular communication in healthy tissue, but also in various diseases. They are of interest to various therapeutic methods.

In short: exosomes are extracellular microvesicles which are released by living cells by means of exocytosis, which contain a multitude of proteins and RNA and which exercise biological functions.

The sole, comprehensive analysis method which leaves exosomes in their natural environment and is capable of evaluating particles with dimensions as small as 20 nm for all possible measurement parameters is NTA or nanoparticle tracking analysis. Said analysis method therefore also has the potential of being able to diagnose the different proteins situated on the surface of the membrane of the exosomes. The detection of different proteins on the surface of the exosomes is achieved using specific molecules known from the immune system. These are antibodies.

Antibodies are highly specific and recognize and bind exclusively to a certain protein.

Thus, if what is wanted is to know whether a certain protein X is present on the surface of an exosome, use is made of an antibody known to specifically recognize the protein X and dock therewith. If the exosome has many of such proteins X, all of said proteins can, in the best case, be recognized and bound by the specific antibodies. If said antibodies have been artificially provided with a fluorescent dye, the entire complex consisting of exosome/antibody/fluorescent dye can be detected by the Zetaview instrument.

If another protein Y is of interest, use is accordingly made of an antibody Y which exclusively recognizes and binds protein Y in a specific manner. If said antibody Y has also been labeled with a fluorescent dye, this exosome/antibody Y/fluorescent dye complex can likewise be visualized in a fluorescence channel. Now, if the Zetaview recognizes a signal in a fluorescence channel, it can be assumed that the relevant exosome bears the protein of interest on its surface.

If no fluorescence signal is visible, the relevant protein does not exist on the surface of the exosome.

Using this apparatus, it is possible, then, to carry out so-called colocalization experiments.

Colocalization means that two or more different proteins are represented side by side on the surface of the exosomes. In our example, these would be protein X and protein Y. What we would thus like to know is whether these two proteins exist side by side on the exosome surface. To this end, it is possible, for example, to label antibody X with a red fluorescent dye and antibody Y with a blue fluorescent dye.

If both labeled antibodies recognize and bind the relevant proteins on the exosome surface, or are represented (colocalized), signals are captured in both fluorescence channels of the ZetaView instrument. If only protein X is represented, a signal is detected only in the red fluorescence channel (because only antibody X can bind), but not in the blue fluorescence channel (and vice versa).

It is thus possible using just a single measurement and a single sample to find out whether different proteins of interest are simultaneously represented (colocalized) on the surface of the exosomes.

In relation to the prior art, what follows is a description of the colocalization analysis of two antibodies on the same exosome by means of an NTA.

DETAILED DESCRIPTION OF THE INVENTION

Figure 1:
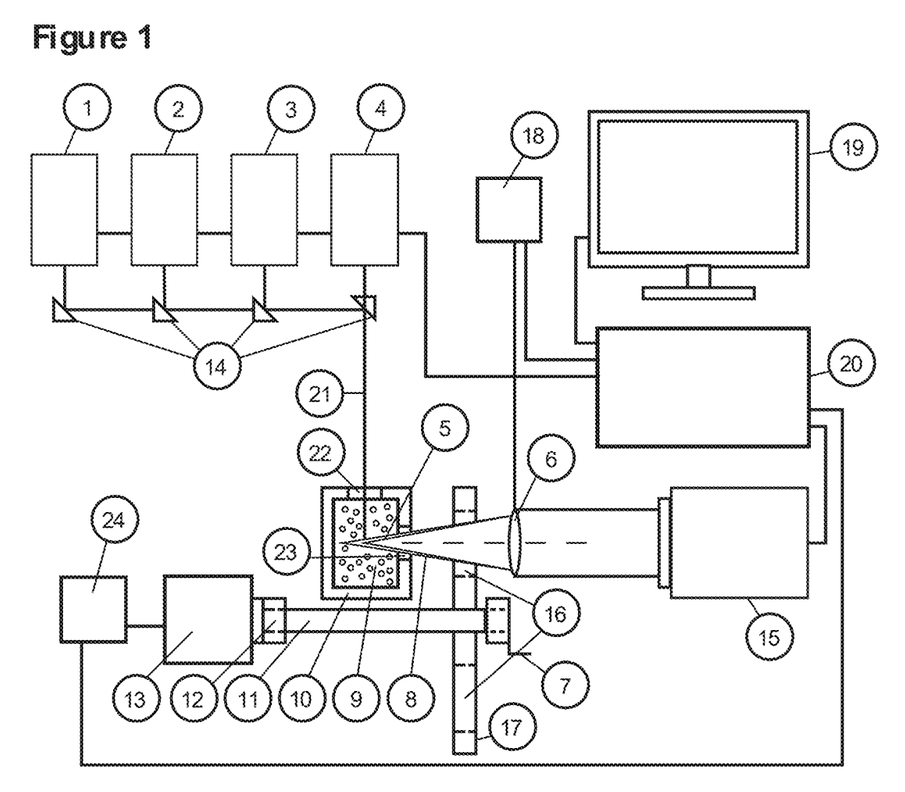
FIG. 1 shows a particular NTA nanoparticle analysis.

FIG. 1 depicts an NTA nanoparticle-tracking measurement arrangement from Particle Metrix that allows the detection of multiple antibodies on the same exosome. For this purpose, it is necessary for multiple combinations of lasers and filters to follow one another in a rapid manner. Since the nanoparticles carry out Brownian motion, they can disappear from the video image after a few seconds, meaning that there are only a few seconds for simultaneous measurement of multiple fluorescences on the very same particle, though in vitro. This means that the laser/filter combination has to change within fractions of a second. Since it is nowadays already possible to guide multiple lasers onto a fiber and to change rapidly from one wavelength to the next by electronic switching, this is no longer a problem. What only remains is to accomplish rapid filter change and to carry out analysis measurement rapidly (within 1 to 10 seconds).

In this form of NTA, the optical system to be imaged consists of an objective having an optionally additional liquid lens 6, which objective is directed to the particulate sample 9 in the measurement cell 10, and a video camera 15 or detector which records the movement of the particles.

The lasers 1 to 4 shown here, as a light source which is intermittently switched via the collection prisms 14 and the beam path 21, serve as an excitatory light source for scattered light and fluorescence light and radiate into the laser pass-through window 22 of the measurement cell 10 at an angle of 90 degrees.

At the camera 15, what is simultaneously registered by means of the control system of the optical system 18 is light from the fluorescence plane 5 and the scattered light plane 8 via the convergent beam path through a combination of microscope objective (not indicated) and liquid lens 6 with adjustable focus. The touchscreen display 19 and the control system containing the particle tracking program 20 are connected to the video camera 15.

In the beam path, in the transverse direction, a change wheel 17 for color filters is arranged on a filter wheel axle 11 and a counterbearing 7 over a change coupling 12 and a filter drive 13, the change wheel being fitted with color filters 16 and the color filter wheel being controlled by means of a device 26. The light which passes through the optical-system pass-through window 23 of the measurement cell 10 and the color filter 16 is guided, via the combination of microscope objective and liquid lens 6, into the video camera 15, where it is registered.

Figure 2:
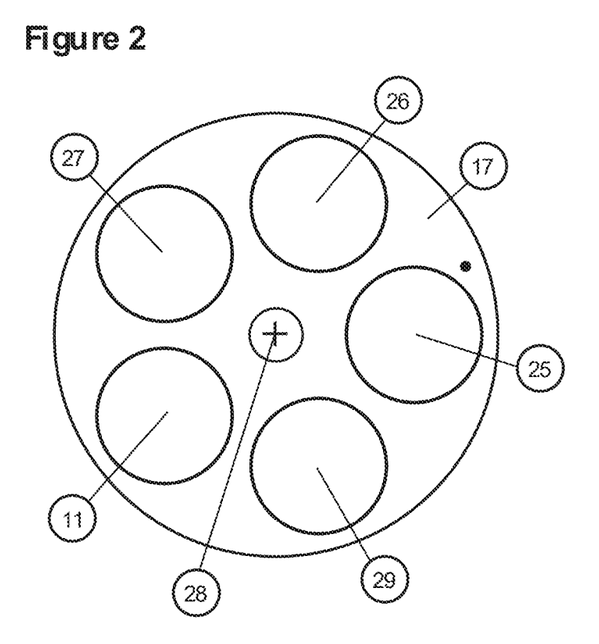
FIG. 2 depicts a change wheel for a color filter 17.

FIG. 2 depicts the change wheel for the color filter 17.

In the center, what can be seen is the filter wheel axle 11 surrounded by the filters 25, 26, 27, 28 and 29. Here, the filter 25 in the form of a quartz glass insert can be considered neutral, whereas the filter numbered 26 opens at a wavelength above 420 nm. The filter numbered 27 opens at a wavelength above 500 nm, the filter 28 opens at a wavelength above 540 nm and the filter 29 opens at 660 nm.

Figure 3:
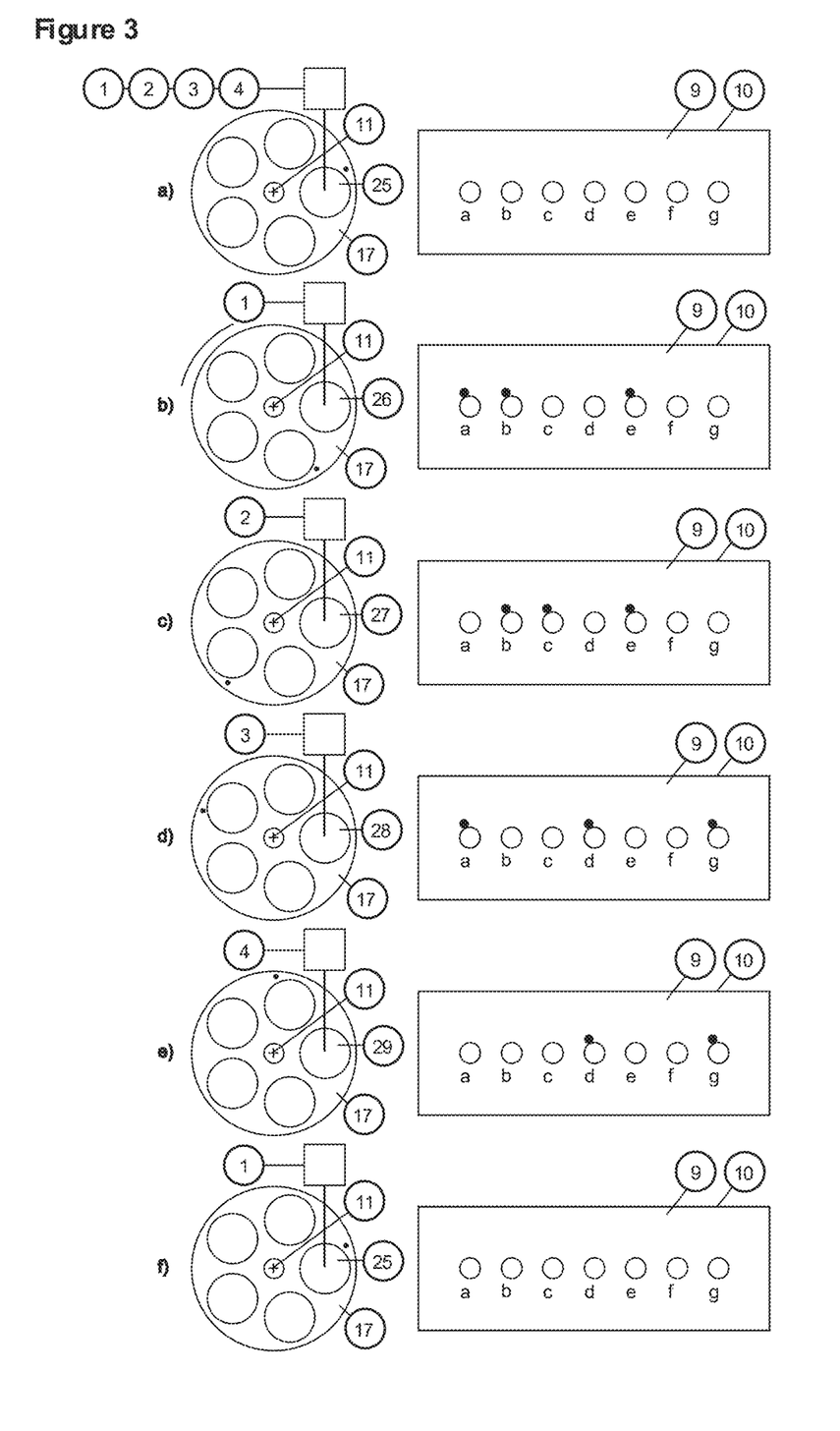
FIG. 3 shows the course of an analysis, multiple lasers and multiple color filters.

FIG. 3 shows the position of the particular color filter for fluorescence emission measurement and of the particular laser in the course of an analysis.

On the left-hand side of FIG. 3, six positions of the color filter 16 are shown by way of example, and at the uppermost position the respectively engaged color filter is indicated by its number and the respectively engaged laser is indicated.

The method of the technique from the prior art shown in FIGS. 1 to 3 can be compared with 2 further methods in order to thus obtain a statement about the quality of the measurements.

It is an object of the present invention to obtain an easy-to-obtain quality control for the described prior art. This is achieved by the method according to claim 1:

a method for determining the fluorescence and the number of antibodies on exosomes using a measurement quality control, comprising the following features:
  a) for preparation for a measurement, a measurement cell (10) is filled with a solution composed of fluorescent antibodies and exosomes as sample (9),
  b) a combination of lasers and filters is used for irradiation of the measurement cell (10) in vitro with rapid changeover and an optical device (15) is used for imaging thereof,
  c) the overall control system for the measurement arrangement that is used is a Particle Metrix measurement arrangement,
  d) a control measurement establishes pattern differences between exosomes without antibody conjugation and those with antibody conjugation,
  e) a further control measurement establishes differences in relation to the prior art by means of an electrophoretic analysis.

Using one instrument and the same measurement cell, the samples from the technique from the prior art are analyzed and compared in two different methods, by the method of pattern recognition and by the method of electrophoresis.

In what follows, the invention will be described in more detail.

Figure 4:
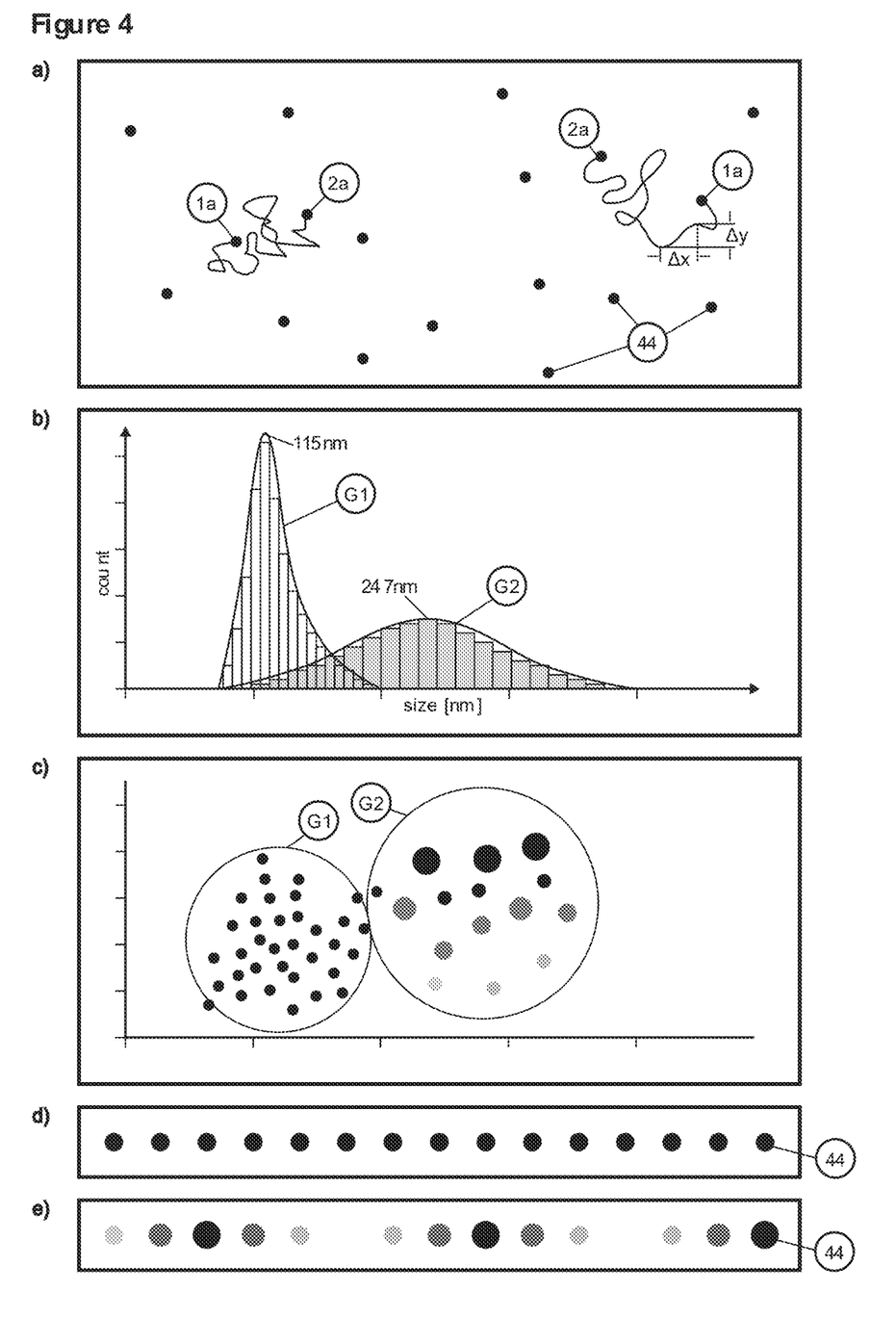
FIG. 4a shows a Brownian motions of particles.
FIG. 4b shows size distribution of the two groups of particles in a bar chart.
FIG. 4c shows a scatter plot from the pattern analysis, depicting the calculated particle size distributions of the two patterns.
FIG. 4d shows the temporal course of a video recording of a particle of group G1.
FIG. 4e shows the temporal course of a video recording of a particle of group G2.

In the figures:

FIG. 4: shows graphs in the monitor 19 due to camera recording and pixel analysis from the pattern recognition for comparison of the measurement from FIG. 1

Figure 5:
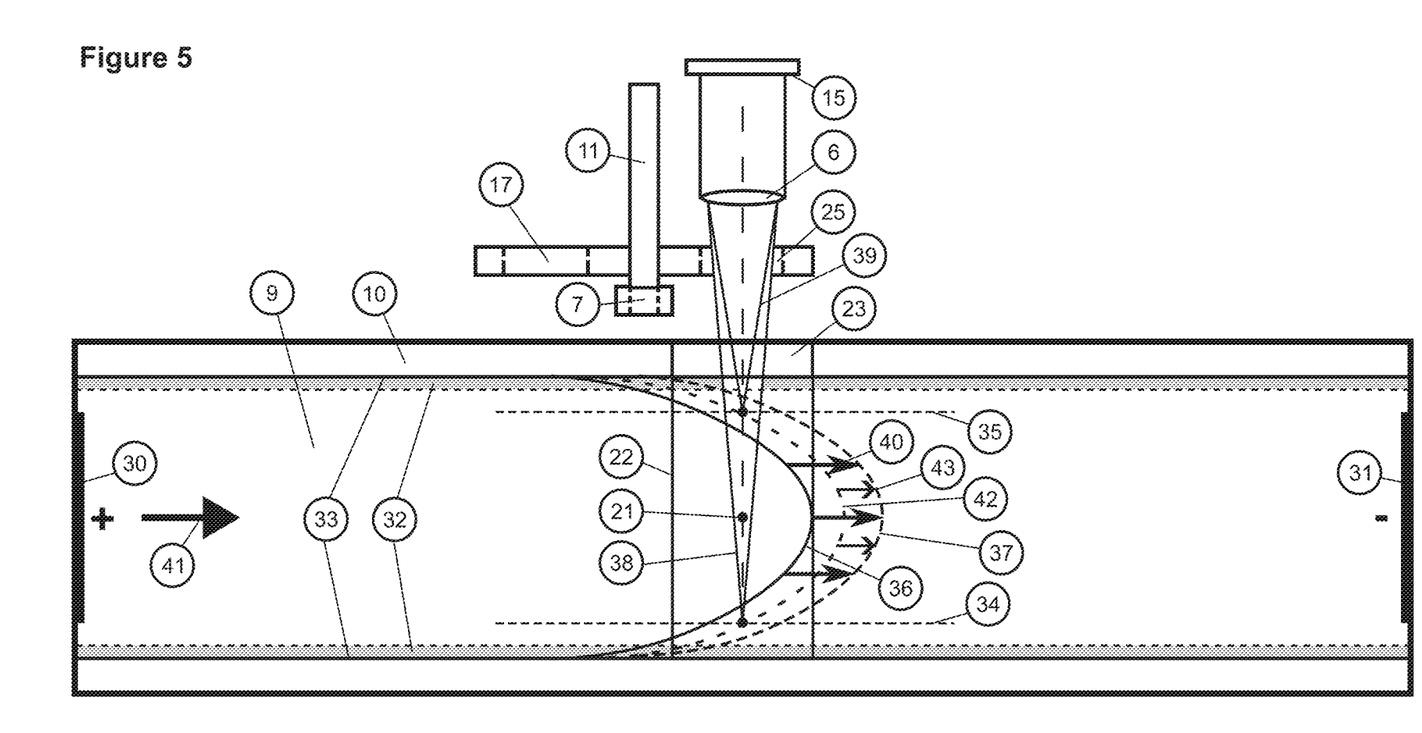
FIG. 5 depicts an electrophoresis and electroosmosis measurement in the measurement cell for comparison of the measurement from the prior art.
Figure 6:
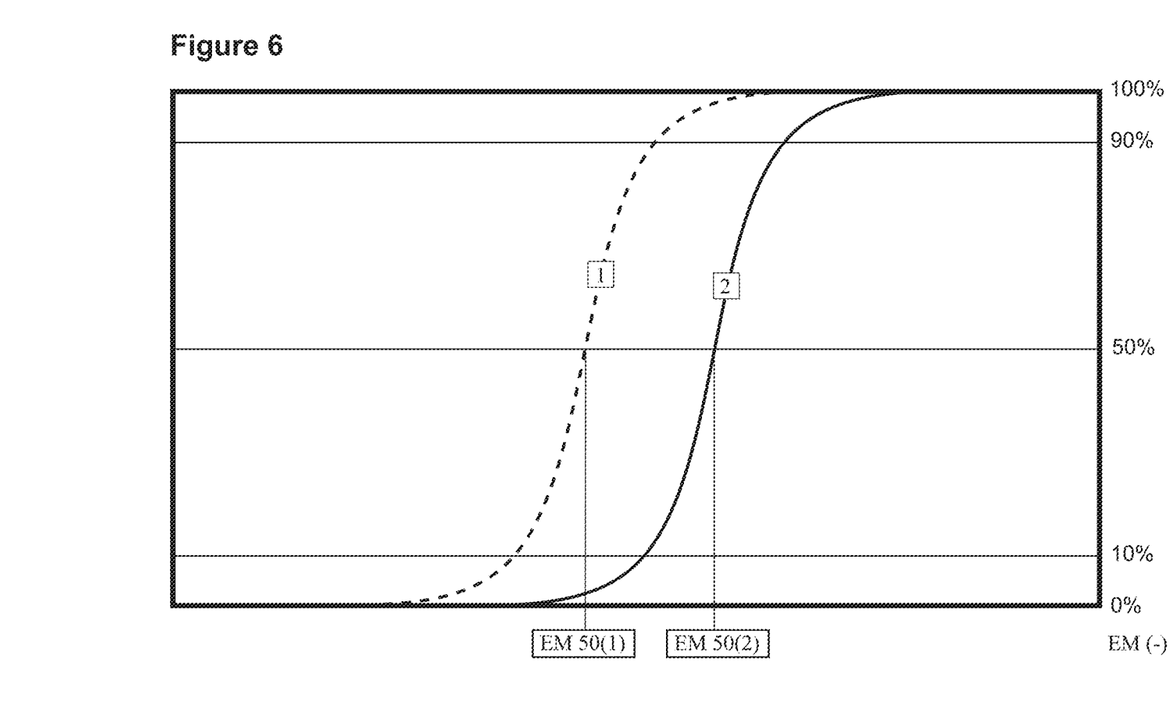
FIG. 6 depicts the cumulative electrophoretic mobility distribution curves of two samples.

FIG. 5: depicts an electrophoresis and electroosmosis measurement in the measurement cell for comparison of the measurement from the prior art FIG. 6: depicts the cumulative electrophoretic mobility distribution curves of two samples

FIG. 4 shows that subgroups of particles (exosomes) can be depicted differently on video. What are meant are groups of exosomes with docked antibodies (proteins) or exosomes without antibodies. In the case of scattered light measurement and of fluorescence light measurement, the subgroups can be calculated by video pattern recognition and presented in graphs. The pattern recognition analysis can be carried out in the scattered light measurement and the fluorescence light measurement and is used for quality control of the technique from the prior art.

FIG. 4*a* shows a video of the Brownian motion of the particles, from which the size follows, the mean square displacement ($\Delta x \cdot \Delta y$) of an individual particle 44 the starting position (1*a*) and the end position (2*a*)—measured in one second and inserted into Stokes' Einstein formula—yields the particle size. The video recording contains additionally further information that is analyzed and evaluated by the pattern recognition program.

These include the brightness, shape, temporal behavior and trajectory lengths of a particle.

FIG. 4*c* shows a scatter plot from the pattern analysis, depicting the calculated particle size distributions of the two patterns.

The example shows the size distribution of exosomes of a HEK293 cell culture, with simultaneous plotting of the temporal behavior of the intensity of each particle (mean intensity) against the size. In the scatter plot, two groups of particles can be seen. Group G1 corresponds to the particle features as depicted in FIG. 4*d*. Group G2 corresponds to the particle features as depicted in FIG. 4*e* (non-exosomes).

From the comparison of group G1 of exosomes measured before the conjugation with antibodies and afterwards, it is possible to deduce pattern differences. As a result, it is possible by means of video pattern recognition to quantify the antibodies on an exosome, i.e., the number of antibodies which have docked with an exosome.

FIG. 4*d* shows the temporal course of a video recording of a particle of group G1.

The particle is small, less bright and its intensity looks uniform over the course of time.

Exosomes are concerned here, since they have a membrane shell, have approximately spherical symmetry and do not flicker.

FIG. 4*e* shows the temporal course of a video recording of a particle of group G2.

The particle is larger and its light flickers between very bright and very dark.

In the example, the "flickering" particles can be excluded as non-exosomes. FIG. 4b shows the size distribution of the two groups of particles in a bar chart. What can be seen here are group G1 as exosomes (115 nm) and group G2 as non-exosomes (247 nm).

The pattern recognition distinguishes the exosomes from other particles and calculates their number in the sample, as shown in FIG. 4c and FIG. 4d. Following a measurement before and after conjugation, the exosomes can be calculated in terms of their size, as shown in FIG. 4a. The difference between the two measurements provides information as to how many antibodies have docked with an exosome.

The result is used for checking of the measurement from technique (prior art) shown in FIG. 1 to FIG. 3.

FIG. 5 shows the schematic depiction of an electrophoretic analysis for particles as a second comparative measurement for the technique from the prior art.

From what is depicted by FIG. 5, it is clear that electroosmosis is triggered by an applied field 41, generated by the plus electrode 30 and minus electrode 31. Its course of movement is depicted by the curve 36.

The electrodes 30, 31 consist of highly conductive graphene in order to produce optimal contact with the suspension in the measurement cell. This avoids interfering bubble formation and the movements of the particles are more homogeneous.

If charged particles are present in the liquid, they move at a velocity v in the electric field E 41. This effect is even across the entire cross section of the cell and is called electrophoresis. What is measured is the electrophoretic mobility $\mu_e=v/E$. Electrophoresis and electroosmosis are independent of one another and add up. The magnitude of the addition is depicted by three arrows 40. The curve 37 shows the course of movement of electroosmosis and electrophoresis $\mu_e$ together in the field 41. The dimension of mobility is reported in µm/s/V/cm. In the case of very high loads, the value displayed by the mobility can be up to 5 µm/s/V/cm.

If what is wanted is to measure the electrophoresis $\mu_e$ independently of the electroosmosis, this must be done in the so-called stationary layers 34 and 35 (SL) of the channel of the measurement cell. At the layers 34, 35, the electroosmosis reverses and is therefore zero. Therefore, at these two layers, it is the electrophoresis alone that is readable. From the geometry of the measurement cell, it is possible to deduce the stationary layers of SL1 34 and SL2 35. The laser radiates into the measurement cell at an angle of 90 degrees to the microscope plane and perpendicularly through the window 22. For measurement, the laser focus 21 and the microscope focus 38, 39 are synchronously alternately directed to SL1, 34 and SL2, 35.

If only the comparisons of the electrophoretic properties, i.e., differences in the ionic loading of the particle surfaces, need to be examined, the can be measured at any desired layer of the measurement cell 10 (along the cell walls). This means that comparisons of the electrophoretic mobility $\mu_e$ can be made at any desired point of the measurement cell, provided that the distance from the cell walls does not change during the comparative measurement. In order to compare pure exosomes and antibody-conjugated exosomes with one another, the ionic conditions of the surrounding liquid (salt type and conductivity) must be identical.

The procedure for a comparative measurement is implemented in 7 steps.

A sample 1+ (without antibody) is compared with a sample 2 (with antibody).

Steps 1-3 is the calibration (sample 1) of the starting point of the measurement.

1st Step:
In a vessel, a certain amount of a suitable liquid is mixed with a certain amount of neutral exosomes.

2nd Step:
In the measurement cell 10, the electrophoretic mobility of sample 1 is measured and a mean value, the EM 50, is calculated. The EM 50(1) is described in more detail in FIG. 6.

3rd Step:
An exact amount of a cationic polymer (reagent) is added to sample 1 and the EM 50 is ascertained as in step 2.

The EM 50(1) is our constant value depicted as curve 37 in FIG. 5 and as curve 1 in FIG. 6. Said value is saved for all further experiments with the suspension of sample 1+. The calibration is completed.

4th Step:
A certain amount containing different fluorescent antibodies is added to a certain amount of the calibrated exosome suspension (sample 1+) and conjugation is measured in the measurement cell 10 by technique 1 (prior art).

5th Step:
At the same time, the EM 50(2) can be ascertained in the measurement cell using the sample from step 4 (exosomes+ antibody). This is depicted by curve 42 in FIG. 5 and by curve 2 in FIG. 6.

6th Step:
The value from step 3 (EM 50(1) calibration) is compared with the value from step 5 (EM 50(2) exosomes+antibody) and the number of antibodies docked on an exosome is calculated.

7th Step:
Comparison of the Measurement Values

By comparing the value from the technique according to the prior art (step 5) and the value from step 6, it is possible to check the quality of the measurement from the prior art.

FIG. 6 shows a graph for the cumulative electrophoretic mobility distribution in % for easier readability of differences in the charge states described by the EM 50(1) of sample 1+ and the EM 50(2) of sample 2 (exosomes+ antibody). What is shown is the change in specific surface charge Q of an exosome upon conjugation with an antibody per surface area F [$C/nm^2$]. More clearly, how many elementary charges x per surface element [$\#e/nm^2$] are lost from the exosomes by binding per µg of antibodies.

The analysis requires complex control of the described method sequences and movement sequences by a specific control and analysis program.

LIST OF REFERENCE SIGNS

1 Laser (violet=405 nm)
2 Laser (blue=488 nm)
3 Laser (green=520 nm)
4 Laser (red=640 nm)
5 Fluorescence plane
6 Liquid lens with adjustable focus
7 Counterbearing of the filter wheel axle
8 Scattered light plane
9 Sample
10 Measurement cell
11 Filter wheel axle
12 Change coupling
13 Filter wheel drive (stepper motor)

14 Collection prisms (all guide lasers into a beam path)
15 Detector or video camera (CCD, CMOS)
16 Color filter (edge filter or bandpass filter)
17 Change wheel for color filters
18 Control system for optical system
19 Touchscreen display
20 Overall control system containing particle tracking program
21 Beam path for laser
22 Laser pass-through window of the measurement cell 10
23 Optical-system pass-through window of the measurement cell 10
24 Control system for color filter wheel
25 Filter, neutral (quartz glass)
26 Filter, opens above 420 nm
27 Filter, opens above 500 nm
28 Filter, opens above 540 nm
29 Filter, opens above 660 nm
30 Field electrode +
31 Field electrode −
32 Counterion layer
33 Inner glass wall of measurement cell (− negatively charged)
34 Stationary layer 1 (SL 1)
35 Stationary layer 2 (SL 2)
36 Curve of purely electroosmotic movement (particles are not charged)
37 Curve of electroosmotic and electrophoretic movement (particles are positively charged), exosomes without antibody (quicker)
38 Focal plane of layer 1 (34)
39 Focal plane of layer 2 (35)
40 Magnitude of electrophoresis v/E
41 Electric field (direction of movement)
42 Curve of electroosmotic and electrophoretic movement, exosomes with antibody (slower)
43 Magnitude between exosomes with and without antibody
44 Particle

I claim:

1. A method for determining the fluorescence and the number of antibodies on exosomes using a measurement quality control, comprising the following features:
   a) for preparation for a measurement, filling a measurement cell (10) with a solution composed of fluorescent antibodies and exosomes as sample (9),
   b) performing a first measurement with a nanoparticle tracking measurement arrangement including a combination of lasers and filters for irradiation of the measurement cell (10) in vitro with rapid changeover and an optical device (15) for imaging thereof,
   c) analyzing images detected by the optical device (15) in the first measurement for detecting the fluorescence and a number of antibodies by nanoparticle tracking analysis,
   d) performing a first comparative measurement by video pattern recognition using the sample, the measurement cell, and the nanoparticle tracking measurement arrangement as used in the first measurement of step b), wherein pattern differences between exosomes without antibody conjugation and those with antibody conjugation are detected, and
   e) performing a video pattern recognition analysis for said first comparative measurement for detecting the number of antibodies, and comparing the number of antibodies detected in the first measurement of step b) with the number of antibodies detected in the first comparative measurement for quality control.

2. The method according to claim 1, further comprising:
   performing a further comparative measurement by means of liquid electrophoresis using the sample, the measurement cell and the nanoparticle tracking measurement arrangement used in the first measurement of step b);
   performing an electrophoretic analysis for the further comparative measurement for detecting the number of antibodies, and
   comparing the number of antibodies detected in the first measurement of step b) and the number of antibodies of the further comparative measurement for quality control.

3. The method as claimed in claim 2, characterized that in the liquid electrophoresis, graphene which is highly conductive for the electrodes is used when choosing the electrodes.

4. The method as claimed in claim 2, wherein, for the liquid electrophoresis:
   a calibration for detecting a first mean value (EM 50(1)) for an exosome suspension without antibodies is performed,
   antibodies are added to the calibrated exosome suspension and a second mean value (EM 50(2)) of the resulting exosome suspension is detected, and
   a number of antibodies is calculated from the first mean value (EM 50(1)) and the second mean value (EM 50(2)).

5. A computer program containing non-transitory program code for carrying out the method steps as claimed in claim 1 when the program is executed in a computer.

6. A computer program containing non-transitory program code for carrying out the method steps as claimed in claim 2 when the program is executed in a computer.

7. A computer program containing non-transitory program code for carrying out the method steps as claimed in claim 3 when the program is executed in a computer.

8. A computer program containing non-transitory program code for carrying out the method steps as claimed in claim 4 when the program is executed in a computer.

9. A machine-readable medium containing the non-transitory program code of a computer program for carrying out the method as claimed in claim 1 when the method is executed in a computer.

10. A machine-readable medium containing the non-transitory program code of a computer program for carrying out the method as claimed in claim 2 when the method is executed in a computer.

11. A machine-readable medium containing the non-transitory program code of a computer program for carrying out the method as claimed in claim 3 when the method is executed in a computer.

12. A machine-readable medium containing the non-transitory program code of a computer program for carrying out the method as claimed in claim 4 when the method is executed in a computer.

* * * * *